US007799817B2

(12) United States Patent
Cremisi

(10) Patent No.: US 7,799,817 B2
(45) Date of Patent: Sep. 21, 2010

(54) COMPOSITIONS AND METHODS FOR SLEEP REGULATION

(75) Inventor: Henry D. Cremisi, Charlotte, NC (US)

(73) Assignee: LifeScape BioSciences Inc, Charlotte, NC (US)

( * ) Notice: Subject to any disclaimer, the term of this patent is extended or adjusted under 35 U.S.C. 154(b) by 1353 days.

(21) Appl. No.: 11/063,253

(22) Filed: Feb. 22, 2005

(65) Prior Publication Data
US 2005/0272690 A1 Dec. 8, 2005

Related U.S. Application Data

(60) Provisional application No. 60/546,151, filed on Feb. 20, 2004.

(51) Int. Cl.
A01N 43/64 (2006.01)
A61K 8/00 (2006.01)
(52) U.S. Cl. ......................................... 514/403; 424/65
(58) Field of Classification Search .................. 514/310
See application file for complete search history.

(56) References Cited

U.S. PATENT DOCUMENTS

| 4,600,723 | A | * | 7/1986 | Short et al. | 514/416 |
|---|---|---|---|---|---|
| 5,230,714 | A | | 7/1993 | Steckel | |
| 5,316,774 | A | | 5/1994 | Eury et al. | |
| 5,403,851 | A | * | 4/1995 | D'Orlando et al. | 514/364 |
| 5,498,423 | A | * | 3/1996 | Zisapel | 424/464 |
| 5,500,225 | A | | 3/1996 | Laudon et al. | |
| 5,654,325 | A | * | 8/1997 | Flaugh | 514/415 |
| 5,707,652 | A | | 1/1998 | Lewy et al. | |
| 5,750,557 | A | | 5/1998 | Zisapel | |
| 5,849,338 | A | | 12/1998 | Richardson et al. | |
| 5,895,652 | A | | 4/1999 | Giampapa | |
| 5,976,568 | A | * | 11/1999 | Riley | 424/451 |
| 6,013,279 | A | | 1/2000 | Klett-Loch | |
| 6,048,846 | A | | 4/2000 | Cochran | |
| 6,048,886 | A | | 4/2000 | Neigut | |
| 6,048,888 | A | | 4/2000 | Zisapel | |
| 6,207,190 | B1 | | 3/2001 | Richardson et al. | |
| 6,281,241 | B1 | | 8/2001 | Elsner | |
| 6,469,044 | B1 | | 10/2002 | Zisapel | |
| 6,521,591 | B1 | | 2/2003 | Smeets et al. | |
| 6,566,389 | B1 | | 5/2003 | Zisapel et al. | |
| 6,620,836 | B1 | | 9/2003 | Patrick | |
| 6,780,884 | B2 | | 8/2004 | Zisapel et al. | |
| 6,833,383 | B2 | | 12/2004 | Zisapel | |
| 6,858,642 | B1 | | 2/2005 | Zisapel et al. | |
| 2001/0006983 | A1 | | 7/2001 | Jia | |
| 2002/0048551 | A1 | | 4/2002 | Keller et al. | |
| 2002/0119191 | A1 | | 8/2002 | Nishino et al. | |
| 2002/0183297 | A1 | | 12/2002 | Niazi | |
| 2002/0183377 | A1 | | 12/2002 | Elsner | |
| 2002/0187108 | A1 | | 12/2002 | Rajaiah et al. | |
| 2003/0012824 | A1 | | 1/2003 | Ott et al. | |
| 2003/0084912 | A1 | | 5/2003 | Pera | |
| 2003/0108624 | A1 | | 6/2003 | Kosbab | |
| 2003/0224071 | A1 | | 12/2003 | Murad | |

FOREIGN PATENT DOCUMENTS

EP 0302582 2/1989

OTHER PUBLICATIONS

"Sleep in America" poll, *National Sleep Foundation*, Washington, D.C., Web-Printout 2002.
"Let Sleep Work for You", *National Sleep Foundation*, Washington, D.C., Web-Printout 2003.
"PALADIN Annual Report", 2002, 11.
"When You Cannot Sleep. ABC's of ZZZs", *National Sleep Foundation*, Washington, D.C., Web-Printout 2003.
Arendt, J. et al., "Melatonin and the Mammalian Pineal Gland", *Chapman & Hall*, Cambridge 1995, 84.
Barinaga, et al., "How the Brain's Clock Gets Daily Enlightenment", *Science*, 295 2002, 955.
Bechtel, W. et al., *Radiology*, 161 1986, 601-604.
Campbell, C. et al., "New York State Nutrition", *Cornell University*, Ithaca, N.Y. 1992, 138.
Cashmore, et al., "Cryptochromes: Blue-light receptors for plants and animals", *Science*, 284 1999, 760-765.
Claustrat, B. et al., "Melatonin and jet lag: confirmatory result using a simplified protocol", *Biol. Psychiatry*, 32 1992, 705.
Czeisler, et al., "Suppression of melatonin secretion in some blind patients by exposure to light", *New England J. Med.*, 332 1999, 6-11.
Green, R. et al., "Editorial: Current concepts in the diagnosis of cobalamin deficiency", *Neurology*, 45 1995, 143-510.
Griffin, et al., "Light-independent role of Cry1 and Cry2 in the mammalian circadian clock", *Science*, 286 1999, 786-71.
Head, KA et al., "Natural therapies for ocular disorders, part two: cataracts and glaucoma", *Altern Med. Rev.* 6(2) Apr. 2001, 141-66.
Herxheimer, et al., "Melatonin for the prevention and treatment of jet lag", *Cochrane Database Syst. Rev.* CD001520 2002.
Hsu, et al., "Putative human blue-light photoreceptors hCRY1 and hCRY2 are flavoproteins", *Biochemistry*, 35 1996, 13871-13877.
Lewy, et al., "Melatonin marks circadian phase position and resets the endogenous circadian pacemaker in humans, since its effect is additive with that of endogenous melatonin", *Circadian Clocks and Their Adjustment, Ciba Foundation Symposium* 183. Wiley, Chichester 1995, 303.
Maquet, P. et al., "The Role of Sleep in Learning and Memory", *Science*, 294 2001, 1048-1052.

(Continued)

Primary Examiner—Sreeni Padmanabhan
Assistant Examiner—Timothy E Betton
(74) Attorney, Agent, or Firm—Kilpatrick Stockton LLP

(57) ABSTRACT

Compositions and methods for the regulation of sleep and circadian rhythms are provided. The compositions are nutritional supplements containing melatonin and one or more vitamins that enhance the effectiveness of melatonin. Preferred vitamins include folic acid, riboflavin (vitamin $B_2$), cobalamin (vitamin $B_{12}$) or pyridoxine (vitamin $B_6$). The compositions beneficially and advantageously regulate sleep when administered to an individual and are administered to a human or animal suffering from an irregular sleep or circadian rhythm or are administered in anticipation of the development of such an irregularity.

23 Claims, No Drawings

OTHER PUBLICATIONS

Palm, et al., "Long term melatonin treatment in blind children and young adults with circadian sleep-wake disturbances", *Dev. Med. Child. Neurol.*, 39 1997, 319.

Provencio, et al., "Photoreceptive net in the mammalian retina", *Nature*, 415 2002, 493-4.

Ritch, R. et al., "Neuroprotection: Is it already applicable to glaucoma therapy", *Current Opin. Opthal.* 11(2) Apr. 2000, 78-84.

Spitzer, et al., "Jet lag: clinical features, validation of a new syndrome-specific scale, and lack of response to melatonin in a randomized, double-blind trial", *Am. J. Psychiatry*, 156 1999, 1392.

Suhner, et al., "Comparative study to determine the optimal melatonin dosage form for the alleviation of jet lag", *Chronobiol. Int.*, 15 1998, 655.

Suhner, et al., "Effectiveness and tolerability of melatonin and zolipidem for the alleviation of jet lag", *Aviat. Space Environ. Med.*, 72 2001, 638.

Tomoda, A. et al., "A school refusal case with biological rhythm disturbance and melatonin therapy", *Department of hild Development, Kumamoto University Medical School, Japan; Brain Dev* 16(1) Feb. 1994, 71-6.

Van Der Horst, G.T. et al., "Mammalian Cry1 and Cry2 are essential for maintenance of circadian rhythms", *Nature*, 398 1999, 626-30.

Zeitzer, et al., "Do plasma melatonin concentrations decline with age?", *Am. J. Med.*, 107 1999, 432.

Zisapel, N. et al., "The use of melatonin for the treatment of insomnia", *Biol. Signals Recept.*, 8 1999, 84.

\* cited by examiner

COMPOSITIONS AND METHODS FOR SLEEP REGULATION

CROSS-REFERENCE TO RELATED APPLICATION

This application claims priority to U.S. Provisional Patent Application No. 60/546,151 entitled "Compositions and Methods for Sleep Regulation" filed Feb. 20, 2004, the entire content of which is incorporated herein by this reference.

FIELD OF THE INVENTION

The present invention relates to nutritional compositions containing melatonin and more specifically relates to melatonin compositions and methods for the regulation of sleep.

BACKGROUND

Sleep, or the natural periodic suspension of consciousness during which the powers of the body and mind are restored, is an essential component of human life. It has long been clear that sleep is crucial for sustaining normal function and the mental and physical well-being of all animals. Common wisdom, partially based on everyday human experiences, and shared by members the scientific and medical communities and laypersons alike, is that sleep is an opportunity for the human body to get much needed repair. The types of repair during sleep include physical repair, such as the repair of torn muscles, organ cleansing, etc., and psychological repair, such as the laying down of memories, working though anxiety, etc.

It is well known that sleep occurs naturally in response to the duration of wakefulness and is regulated by a number of brain processes. The longer a person is awake, the stronger their desire to sleep. However, it is the brain that controls the timing of sleep and wakefulness during the day-night cycle through a physiological mechanism generally referred to as a circadian, or biological, clock (see, for example, "Let Sleep Work for You", *National Sleep Foundation*, Washington, D.C. (2003)). Daily biological rhythms, including sleep-wake cycles, are generally referred to as circadian rhythms. Circadian clocks are known to exist in mammals, plants, fungi, insects, etc., and run on approximately a 24 hour cycle that corresponds to the day-night cycle of the Earth. The molecular mechanisms underlying biological clocks are best understood in *Drosophila*, a fruit fly, and involve a light-sensitive protein cryptochrome, and a complex system of proteins whose transcription, translation, and degradation are intricately regulated in response to daylight or the absence of daylight.

In mammals, the process is less well understood than in other organisms. However, it has been established that the master clock mechanism in mammals is associated with the suprachiasmatic nucleus (SCN), a distinct group of around 10,000 cells located in the hypothalamus of the brain. Peripheral clocks, located in every cell, are regulated by the SCN. Light receptors in the retina are connected to the SCN through a pathway called the retinohypothalamic tract. Recent studies suggest that the light receptors receive signals from the retinal cells (rods and cones) and pass the signals on either to vision areas of the brain or directly to SCN. The SCN then sends the signals to clocks in the rest of the body. Both cryptochrome and melanopsin proteins have been suggested as the candidate light sensitive proteins in mammals. However, the circadian pathways of a mammalian brain, including that of *Homo sapiens*, remain to be deconvoluted (Barinaga, "How the Brain's Clock Gets Daily Enlightenment" *Science* 295:955 (2002)).

Thus, in spite of a familial and persuasive presence of sleep in human life and an extensive body of sleep research, the details of sleep regulating machinery remain unknown at this time. Interestingly, the exact function of sleep is also considered to be unknown, even though sleep has been implicated, for example, in the plastic cerebral changes that underline learning and memory (Maquest, "The Role of Sleep in Learning and Memory" *Science* 294:1048-1052 (2001)). Also, the so-called "sleep architecture", or predictable patterns of brain activity alternating approximately every 90 minutes between REM (rapid-eye movement) and NREM (non-rapid eye movement) sleep throughout a typical eight hour period are well known, as is the fact that both REM and NREM states are important for experiencing quality sleep.

While the exact mechanisms regulating sleep in humans may not be revealed for many years, methods and tactics for treating sleep disturbances and problems must be addressed on a day-to-day basis for a significant number of individuals who require continuous and restorative sleep in order to feel refreshed and alert during their wakeful periods of time.

Sleep disturbances are common in humans and lead to a variety of physical and mental problems in a significant portion of the population. The 2002 National Sleep Foundation (NSF) "Sleep in America" poll revealed that 74 percent of American adults experience a sleeping problem a few nights a week or more. According to some sources, 32 percent of Persian Gulf War veterans listed sleep disturbance as one of their top seven maladies after returning from the Persian Gulf. Sleep disruptions lead, for example, to pain, fatigue, memory and thinking difficulties, difficulty maintaining alertness, lack of energy, irritability and, a generally impaired mood with difficulty handling stress. Lack of sleep also puts one at risk for injury and accidents, such as those caused by falling asleep while operating machinery, with approximately 100,000 sleep-related vehicle crashes resulting in approximately 1,500 deaths each year. In addition, disrupted sleep leads to poor performance at work, difficulty getting along with others, problems completing a task, poor concentration, inability to make decisions and an increase in the frequency of unsafe actions. Insufficient sleep may also make it difficult to exercise and can reduce the benefit of hormones released during sleep. In addition, inadequate amounts of sleep suppress the immune system, thereby increasing susceptibility to disease and, according to some research, increase the risk of developing obesity and diabetes and impact aging ("Let Sleep Work for You", *National Sleep Foundation*, Washington, D.C. (2003)). Productivity lost due to sleepiness has been estimated to cost the national economy as much as 100 billion annually ("When You Cannot Sleep. ABCs of ZZZs, *National Sleep Foundation*, Washington, D.C. (2003)).

It is commonly known and reported by authoritative sources, such as those published by the National Sleep Foundation, that causes of sleep disruptions are multiple and varied (see, for example, When You Cannot Sleep. ABCs of ZZZs, *National Sleep Foundation*, Washington, D.C. (2003), excerpts of which are quoted in this section). One group of causes is psychological factors, with stress being the primary cause of short-term sleeping difficulties. Common triggers include school- or job-related pressures, a family or marriage problem, and a serious illness or death in the family. While most sleep problems disappear when the stressful situation is over, if short-term sleep problems are not managed properly, they can persist long after the original stress has passed. Another common group of causes are lifestyle stressors, including consumption of alcohol or caffeine and other stimulants, exercising close to bedtime, following an irregular morning and nighttime schedule, and working or doing other mentally intense activities right before or after getting into bed.

A further source of sleep disturbances includes disruptions of the normal day-night cycle, such as shift work and jet lag, which often cause disturbances in the circadian rhythms. Approximately 20 percent of employees in the United States are shift workers. They are two to five times more likely than employees with regular, daytime hours to fall asleep on the job. The term "jet lag" is commonly used to refer to an inability to sleep caused by travel across several time zones. Among other sleep disruptors are environmental interferences, such as a room that is too hot, cold, noisy or brightly lit, interruptions from children or other family members, or excessive noise. Environmental factors are often particularly troublesome for persons involved in active military actions or hospital patients.

A number of physical problems also interfere with the ability to fall asleep or stay asleep. For example, arthritis and other conditions that cause pain, backache, or discomfort can make sleeping difficult. In post-surgical recovery, sleep disruptions due to pain and discomfort present a particular problem because interrupted sleep is believed to interfere with healing. Disorders that cause involuntary limb movements during sleep, such as Restless Legs Syndrome, break up normal sleep pattern and are also likely to make sleep less refreshing, resulting in daytime sleepiness. For women, pregnancy and hormonal shifts including those that cause premenstrual syndrome (PMS) or menopause and its accompanying hot flashes can intrude on sleep. In addition, certain medications such as decongestants, steroids and some medicines for high blood pressure, asthma, or depression can cause sleeping difficulties as an adverse side effect.

According to the National Sleep Foundation certain individuals are particularly vulnerable to disrupted sleep, including, but not limited to, students, shift workers, travelers, and persons suffering from acute stress, depression, or chronic pain ("When You Cannot Sleep. ABCs of ZZZs, *National Sleep Foundation*, Washington, D.C. (2003)). Employees working long hours or multiple jobs may find their sleep less refreshing. Teenagers can have difficulty falling asleep until late at night and some awaken early the following morning. Many young adults keep relatively irregular hours and, as a group, report higher rates of dissatisfaction with the sleep obtained. Obesity and excessive body weight also increase the risk of insomnia.

Older adults also have frequent difficulty with sleep. With advanced age, the total amount of sleep needed in a 24 hour period is not reduced, but common sleep disruptors, such as impaired health, pain and the increased use of medications are prevalent. In older adults, sleep-wake cycle disturbances and circadian-based sleep imbalances are also widespread. Reduced endogenous melatonin production that is secondary to the process of aging can cause these sleep disruptions.

In view of the foregoing, it is evident that sleep disturbances are a prevalent and serious problem in the human population. Sleep disturbances are currently counteracted using a variety of resources and approaches, including lifestyle modifications, behavioral treatments, medications and nutritional supplements. Prescription drug medications that promote sleep include hypnotics, anti-depressants, and anti-anxiety drugs. All of the available prescription medications can cause serious side effects such as, for example, rebound insomnia, which occurs when a person stops taking a prescribed medication and experiences one or two nights of insomnia that are worse than those experienced before treatment. Another side effect to medical treatment with is the development of an addiction to the medication. The beneficial effects of a drug prescribed for insomnia may not subside when desired resulting in day-time sleepiness, impairment of concentration, and excessive sedation. Also, certain anti-insomnia medications cannot be combined with other sedatives, such as alcohol, and should be avoided by people with certain medical conditions. Sleep aids that are available without a prescription, or "over-the-counter" (OTC) sleep promoters, such as antihistamines and pain-relievers, promote sleep by virtue of their sedative properties, but are prone to many of the same undesirable side effects as prescription sleep aids.

Among the currently available selection of non-prescription sleep aids are certain nutritional supplements. When administered, usually by oral ingestion, these nutritional supplements provide an increased amount of a substance either occurring naturally in a human body or commonly contained in a food consumed by humans. One such nutritional supplement is melatonin, which is the principal product of the mammalian pineal gland. Melatonin acts as an internal representative of nighttime. Production is confined to the hours of darkness both by an appropriately phased circadian rhythm of pineal stimulation and by an extreme sensitivity of pineal melatonin synthesis to inhibition by light (J. Arendt, MELATONIN AND THE MAMMALIAN PINEAL GLAND [Chapman & Hall, Cambridge, 1995]). The production of melatonin is induced by the perception of darkness as transmitted from the eyes to the pineal gland between the two hemispheres of the brain. The pineal gland of a normal person produces approximately 500 mcg (micrograms) of melatonin daily. However, starting at age 12, or even earlier, production of this key hormone goes into steady decline. In an octogenarian the amount of melatonin produced is quite nominal. Reduced endogenous melatonin production can cause sleep-wake cycle disturbances and circadian-based sleep imbalances.

Melatonin is currently available commercially as a treatment for insomnia. In the United States, it is available without a prescription, in sublingual and tablet form. Unfortunately, the results of various studies conducted to ascertain the sleep-promoting properties of the currently available melatonin compositions have been inconsistent and many lack objective criteria for ascertaining sleep improvements. Studies that have contained objective criteria failed to show that melatonin is demonstrably beneficial for promoting sleep.

In view of the foregoing, there is a clear, unrealized need for sleep regulating treatments, specifically effective treatments that promote healthful sleep and counteract sleep disturbances without causing adverse side effects such as rebound insomnia, excessive sedation, inappropriate sleepiness, loss of concentration, or formation of habit. Particularly, compositions are needed that reliably, consistently, and beneficially regulate sleep or circadian rhythms, or both, in an individual, such as a human or an animal. Compositions that regulate sleep in patients with sleep-wake cycle disturbances and circadian rhythm imbalances are desired. Compositions that induce sleep, as well as those that help a patient remain asleep are needed. Older adults are in particular need of such compositions. Also, older adults are in need of the compositions that would help counteract reduced endogenous melatonin production associated with aging.

SUMMARY

The present invention addresses the above unrealized needs by providing compositions and methods of using the compositions for the regulation of sleep and circadian rhythms. The compositions described herein are nutritional supplements containing melatonin and one or more vitamins that enhance the effectiveness of melatonin. Preferred vitamins include folic acid and riboflavin (vitamin $B_2$). The preferred compositions contain both folic acid and riboflavin. Optionally, the compositions also contain cobalamin (vitamin $B_{12}$) or pyridoxine (vitamin $B_6$), or both.

The compositions described herein, when administered to a human or animal, beneficially and advantageously regulate sleep and promote the establishment and maintenance of circadian, or biological, rhythms. Such rhythms include an ability to sleep and stay awake according to an actual or designated day-night cycle. In some embodiments, the compositions are administered to a human or animal suffering from an irregular sleep or circadian rhythm or may be administered in anticipation of the development of such an irregularity. In one embodiment, the compositions described herein may be administered to older adults suffering from sleep-wake cycle imbalances and circadian rhythm disturbances. In another embodiment, the compositions are administered to counteract reduced endogenous melatonin production associated with aging. In one aspect of the present invention, the compositions described herein counteract a melatonin deficiency associated with aging. In another aspect, the compositions simultaneously counteract melatonin and vitamin deficiencies associated with aging. Thus, in some embodiments, the compositions are useful for counteracting fundamental deficiencies of the aging population.

The compositions described herein, when administered to a human or an animal, induce sleep, maintain sleep, or both. When administered to an individual, the compositions regulate sleep and circadian rhythms more reliably and consistently than melatonin alone. The combination of melatonin and vitamins reduces variations in bioresponsiveness and facilitates a biological response to the melatonin. In one embodiment, the composition facilitates the biosynthesis of endogenous melatonin.

Furthermore, in some aspects and embodiments, the compositions are more quickly and more efficiently processed after administration than the conventional compositions. The compositions induce sleep quicker, more efficiently, or more consistently, or any combination thereof, than the conventional compositions. In other aspects and embodiments, the compositions are time-delayed, delayed release, or slow-release formulations. In the time-delayed formulations, the active ingredients to are coated to delay their release, for example, in the digestive tract and avoid rapid first-pass metabolism by the liver, thus ensuring more active ingredient to the target site. The delayed release of the active ingredients assures sleep maintenance.

In a preferred embodiment, melatonin, riboflavin and folic acid are combined. In another preferred embodiment, melatonin, cobalamin, and pyridoxine are combined. In one more preferred embodiment, melatonin, riboflavin, cobalamin and pyridoxine are combined. In one aspect, the compositions are formulated to contain high doses of cobalamin. The combination provides an unexpected, novel, and beneficial synergistic effect in that smaller quantities of melatonin are administered to achieve the same or an enhanced sleep-regulating effect when compared with the amounts of melatonin provided in currently available nutritional supplement compositions and the effects they achieve.

The present invention also provides a method for regulating sleep or circadian rhythms in a human or animal comprising administering to the human or animal a novel nutritional composition comprising melatonin and a vitamin, such as, but not limited to, cobalamin, folic acid, riboflavin, or pyridoxine. The composition can be a rapid-release or a delayed release composition, and comprise various inactive ingredients, coatings, or shells. The method of regulating sleep or circadian rhythms provided herein is a method of inducing sleep, maintaining sleep, or both. The method can also advantageously affect the ability of a human or an animal to be awake, alert, or both, when not sleeping. The method can also advantageously regulate the ability of a human or an animal to fall asleep, wake up, or both, on a desired schedule.

The present invention also provides a method of regulating a biological response of a human or an animal to melatonin comprising administering to the human or animal a composition comprising melatonin, cobalamin and a vitamin, wherein the vitamin is folic acid, riboflavin, or pyridoxine. A method of advantageously affecting synthesis or utilization, or both, of melatonin in a human or an animal, comprising administering novel compositions disclosed herein, is also within the objects and embodiments of the present invention. A method of counteracting age-related decrease in endogenous melatonin production in a human or an animal by administering novel compositions disclosed herein is also envisioned and falls within the scope of the present invention.

Also provided is a method of modulating activity of melatonin in a nutritional composition, comprising combining melatonin and a vitamin in the composition. The suitable vitamins include, but are not limited to, cobalamin, folic acid, riboflavin, or pyridoxine. Activity of melatonin in a nutritional composition can be further modulated by addition of inactive ingredients, coatings, and the like.

These and other objects of the present invention will become apparent after reading the following detailed description of the disclosed embodiments and the appended claims.

DETAILED DESCRIPTION OF THE PREFERRED EMBODIMENTS

Compositions and methods of using the compositions for the regulation of sleep and circadian rhythms are provided. The compositions described herein are nutritional supplements that contain melatonin and one or more vitamins that enhance the sleep regulating or circadian rhythm regulating effectiveness of melatonin. Preferred vitamins include folic acid (a member of the vitamin B complex) and riboflavin (vitamin $B_2$). More preferably, the compositions contain melatonin, folic acid and riboflavin. Embodiments of the nutritional compositions also contain the vitamins cobalamin (vitamin $B_{12}$), pyridoxine (vitamin $B_6$), or a combination of both. In a preferred embodiment, the nutritional compositions contain melatonin, folic acid, riboflavin, cobalamin, and pyridoxine. The nutritional compositions also contain, in any combination, fillers, diluents, or disintegrants, or other inactive ingredients. The nutritional compositions are formulated as conventional, rapid-release, or delayed-release formulations. Accordingly, the compositions can comprise the agents facilitating the release or slowing the release of the ingredients.

In accordance with the methods, the compositions described herein are administered to a human or animal by conventional routes of administration in any manner known to those skilled in the art. Preferably, the compositions are in tablet or capsule form and are administered orally. The compositions are administered in a sufficient amount to beneficially and advantageously regulate sleep or circadian rhythms. The compositions may be administered to a human or animal suffering from an irregular sleep or may be administered in anticipation of the development of such an irregularity. The compositions can be administered to counteract sleep-wake cycle imbalances or circadian rhythm disturbances, or both, associated with aging, shift work, jet lag, or any other cause. In one aspect, the compositions are administered to counteract sleep disturbances associated with aging. In another aspect, the compositions are administered to counteract melatonin deficiency associated with aging. In some embodiments, compositions provide melatonin nutritional supplementation. In other embodiments, compositions provide nutritional supplementation to assist endogenous melatonin synthesis. In other embodiments, the compositions facilitate utilization and effects of the endogenous or supplemental melatonin. The compositions also counteract vitamin deficiencies, provide beneficial vitamin supplementation, or both.

As used herein, the term "sleep regulation" denotes modulation of sleep in any manner, including, but not limited to, an ability to fall asleep, stay asleep for a certain period of time, particularly for a period of time required to achieve the benefit of restorative qualities of sleep, ability to sleep according to a normal sleep cycle comprising REM and non-REM sleep, or any combination of the foregoing.

In another aspect, the compositions described herein beneficially and advantageously promote the establishment and maintenance of circadian, or biological, rhythms in an individual. Such rhythms include but are not limited to, an ability to sleep and stay awake according to an actual or designated day-night cycle. In particular, the compositions described herein beneficially and advantageously help to establish and maintain circadian rhythms and sleep-wake cycles in individuals whose rhythms and cycles are disturbed due to any physiological, psychological, or lifestyle cause, including, but not limited to, aging, jet lag, shift work, irregular schedule, anxiety or depression.

The compositions described herein regulate sleep and circadian rhythms more reliably and consistently when administered to an individual than conventional nutritional supplement compositions containing melatonin alone. The combination of melatonin and vitamins, particularly riboflavin and folic acid, reduces variations in bioresponsiveness observed in individuals currently receiving conventional melatonin tablets and facilitates a biological response to the melatonin. Furthermore, in some embodiments, the compositions provided herein are more quickly and more efficiently processed by the human body after administration, thereby facilitating efficient induction of sleep. In other embodiments, compositions are time-delayed, delayed release, or slow-release formulations. In the time-delayed formulations, the active ingredients are coated to delay their release, for example, in the digestive tract and avoid rapid first-pass metabolism by the liver, thus ensuring more active ingredient to the target site. The delayed release of the active ingredients facilitates sleep maintenance. Both fast-release and delayed-release components can be combined in the same composition.

Melatonin Composition

Although not wishing to be bound by the following, it is believed that the unique combination of melatonin and the one or more of the vitamins described herein synergizes both the light-dependent and light-independent circadian pathways. Therefore, the compositions and methods provided herein are highly efficient, and less melatonin is needed to achieve the desired therapeutic effect when compared with conventional melatonin dietary supplements. The preferred concentration of melatonin in the composition to be administered to a human adult is less than 5 mg by weight.

Photoreceptors are specialized body sensors that respond or elicit a response to light stimuli. Vision is mediated in the mammalian eye by photoreceptors (rods for black and white vision) and cones (color vision). Photoreceptors have additionally been identified that synchronize the innate circadian rhythm to the solar light-dark cycle. (Provencio, I, Rollag, M. D., Castrucci, A. M., Photoreceptive net in the mammalian retina, *Nature* 415:493-4 (2002); van der Horst, G. T. J., Muitjens, M., Kobayashi, K, et al. Mammalian Cy1 and Cry 2 are essential for maintenance of circadian rhythms, *Nature* 398:626-30 (1999); Griffin, E. A., Jr., Staknis, D., Weitz, C. J., Light-independent role of Cry1 and Cry2 in the mammalian circadian clock, *Science* 286:768-71 (1999). These receptors are quite distinct receptors from those mediating vision. These photoreceptors receptors are composed of a protein (melanopsin) and the light sensitive prosthetic groups, methyltetrahydrofolate (MTHF) and flavin adenosine dinucleotide. (Hsu, D. S., Zhao, X., Zhao, S, Putative human blue-light photoreceptors hCRY1 and hCRY2 are flavoproteins. *Biochemistry* 35:13871-7 (1996)) The methyltetrahydrofolate serves the function of light harvesting and the flavin participates in the redox reaction ion light-dependent circadian rhythmicity. (Cashmore, A. R., Jarillo, J. A., Wu, Y.-J., Liu, D., Cryptochromes: Blue-light receptors for plants and animals, *Science* 284:760-65 (1999))

Melatonin has been approved by the U.S. Food and Drug Administration (FDA) for the treatment of sleep disorders in patients lacking light perception. (Czeisler, C. A., Shanahan, T. L., Klerman, E. B., et al, Suppression of melatonin secretion in some blind patients by exposure to light. *New England J Med* 332:6-11 (1999); Palm, L., Blennow, G., Wetterberg, L., Long term melatonin treatment in blind children and young adults with circadian sleep-wake disturbances. *Dev. Med. Child Neurol.* 39:319 (1997)) The pharmacologic dosing of melatonin provides a light-independent circadian prompt. In other words, when patients lacking light perception are treated with a dose of melatonin, the body acts as if light is absent and sleep is induced. (Sancar, A., Cryptochrome: the second photoactive pigment in the eye and its role in circadian photoreception. *Ann. Rev. Biochem.* 69:31-67 (2000)) In normal individuals, melatonin levels increase during the night and decrease during the day. This natural surge of melatonin concentrations in the body in the absence of daylight facilitates the onset of sleep.

Melatonin is the principal sleep-regulating hormone in the body. It is normally excreted with day/night cycles. Between the ages of 20 and 70, adults experience about a 37% decline in daily melatonin output. (Zeitzer, J. M., Daniels, J. E., Duffy, J. F., et al. Do plasma melatonin concentrations decline with age? *Am. J. Med.* 107:432 (1999). Thus, melatonin deficiency is a fundamental deficiency associated with aging. Melatonin supplementation beneficially addresses this deficiency in general, and, more specifically, mitigates the sleep-wake cycle disturbances and circadian-based sleep imbalances associated with the age-related reduction of endogenous melatonin production.

As a supplement, melatonin exhibits both phase-shifting and sleep promoting properties. (Zisapel, N. The use of melatonin for the treatment of insomnia. *Biol. Signals. Recept.* 8:84 (1999); Suhner, A, Schlagenhauf, P, Hofer, I, et al. Effectiveness and tolerability of melatonin and zolipidem for the alleviation of jet lag. *Aviat. Space Environ. Med.* 72:638 (2001)) Exogenous melatonin taken in the late afternoon will generally produce a phase advance (moves the body clock forward) (Lewy, A. J., Sack, R. L., Blood, M. L., et al. Melatonin marks circadian phase position and resets the endogenous circadian pacemaker in humans, since its effect is additive with that of endogenous melatonin. (In: CIRCADIAN CLOCKS AND THEIR ADJUSTMENT, Ciba Foundation Symposium 183.

Wiley, Chichester (1995). p. 303)) However, when administered in the early morning, exogenous melatonin will cause a phase delay (moves the body clock backward) by antagonizing the effect of bright light.

Because melatonin has been available without a prescription in many countries as a dietary supplement and has not been targeted to be a commercially successful pharmaceutical product, few studies of melatonin have been funded. As such there is a relatively limited data on efficacy, dose, timing, and side effects. However, a systematic review was conducted to analyze ten randomized, placebo-controlled trials (RCTs) that assessed the effect of melatonin on jet lag (Herxheimer, A, Petrie, KJ. Melatonin for the prevention and treatment of jet lag. *Cochrane Database Syst. Rev.* CD001520 (2002)). Eight of these trials found less jet lag after melatonin administration. Four trials reported global jet lag scores (0=no jet lag, 100=extreme jet lag) that could be combined: melatonin reduced the mean score for eastward flights (31 versus 51 after placebo; absolute reduction of 20 [95 percent CI –28 to –11]); for westward flights (two RCTs) melatonin also reduced the mean score (22 versus 41 after placebo; absolute reduction of 19 [95 percent CI –27 to –7]). The two studies in the systematic review showing no benefit with melatonin may have had methodologic problems with patient selection and timing of outcome assessment.

Most trials of melatonin have used doses containing 5 mg or more. A study utilizing an 8 mg dose had similar results to those using 5 mg (Claustrat, B., Brun, J., David, M., et al. Melatonin and jet lag: confirmatory result using a simplified protocol. *Biol. Psychiatry*. 32:705 (1992)). One study, comparing doses of 5 mg and 0.5 mg (fast release) found that the lower dose was almost as effective as the higher dose for symptoms of jet leg unrelated to sleep. However, the higher dose had a greater effect on sleep quality and sleep latency than the lower dose. Slow release melatonin (2 mg) was less effective than either 5 mg or 0.5 mg (fast release), suggesting that a melatonin pulse is important for efficacy. (Suhner, A., Schlagenhauf, P., Johnson, R., et al. Comparative study to determine the optimal melatonin dosage form for the alleviation of jet lag. *Chronobiol. Int.* 15:655 (1998)).

Side effects of melatonin reported in trials include daytime sleepiness, dizziness, headache, and loss of appetite. However, it is difficult to know whether these were actual drug side effects or were symptoms of the underlying jet lag. "Heavy head," disorientation, nausea, and unspecified gastrointestinal problems were also noted. In one study, a man developed difficulty in swallowing and breathing twenty minutes after the first dose of melatonin. (Spitzer, R. L., Terman, M., Williams, J. B., et al., Jet lag: clinical features, validation of a new syndrome-specific scale, and lack of response to melatonin in a randomized, double-blind trial. *Am. J. Psychiatry* 156:1392 (1999)).

Melatonin is included in the compositions described herein based on historical safety and efficacy results such as those described above. However, the concentrations of melatonin in the compositions described herein are generally lower than those commonly present in conventional melatonin dietary supplements and are preferably 5 mg or less by weight. Therefore, the melatonin compositions described herein exhibit fewer side effects. It has been unexpectedly discovered that a lower concentration of melatonin will achieve or exceed the beneficial effect observed upon administration of conventional concentrations in melatonin supplements (5 mg or more) if the melatonin is combined with particular vitamins, as described herein.

Folic acid, or folate, is included in a preferred embodiment of the composition described herein at a level to ensure adequate folate availability in the setting of substantial dietary inadequacy. Numerous studies have documented the presence of insufficient dietary folate due to losses in food preparation, storage, vitamin-mineral-drug interactions, as well as the concurrence of sleep disorders and folate deficiency in the elderly. (Campbell, C. "New York State Nutrition" Cornell University, Ithaca, N.Y. (1992))

In a preferred composition, cobalamin (vitamin $B_{12}$) is included. In one aspect, cobalamin supplementation precludes masking of $B_{12}$ deficiency than can occur with folate replacement. In one embodiment, cobalamin supplementation precludes pernicious anemia. Pernicious anemia typically is caused by the diminution or absence of stomach acid secretion, with consequent failure of the gastric mucosa to secrete the intrinsic factor necessary for the absorption of vitamin $B_{12}$, characterized by a great reduction in the number of red blood cells and an increase in their size. Folate supplementation can mask pernicious anemia in a patient. Administering cobalamin together with folate addresses this problem.

In one embodiment, pyridoxine is included to preclude diminished cobalamin absorption as well as low blood and hepatic levels, which are seen in pyridoxine deficiency. The incorporation of both cobalamin and pyridoxine in a preferred embodiment of the composition described herein limits the likelihood of a catastrophic neurological event such as subacute combined degeneration of the dorsal and lateral spinal columns (Green, R., Kinsella, L. J. Editorial: Current concepts in the diagnosis of cobalamin deficiency. *Neurology* 45:143-510 (1995)). This lesion is specific for cobalamin deficiency, and may present acutely if folate is replete without cobalamin.

The inclusion of pyridoxine in a preferred embodiment of the composition described herein enhances normal melatonin synthesis, in which pyridoxine is important as a cofactor. Consequently, pyridoxine deficiency inhibits melatonin synthesis. Therefore, drugs that deplete pyridoxine may also inhibit melatonin synthesis. Such drugs include oral contraceptives, estrogens, hydralazine, loop diuretics, penicillamine and theophyline. In addition, beta-blockers and benzodiazepines may deplete melatonin by enzyme inhibition.

Active Ingredients

As used herein, the term "active agent" or "active ingredient" is a component of a dosage form that performs a biological function when administered or induces or affects (enhances or inhibits) a physiological process in some manner. "Activity" is the ability to perform the function, or to induce or affect the process. Active agents and ingredients are distinguishable from excipients, such as carriers, vehicles, diluents, lubricants, binders, disintegrants, fillers, and other formulating aids, and encapsulating or otherwise protective components.

An inactive ingredient is any component of a dosage form other than the active ingredient. It is to be understood that inactive ingredients can modulate the behavior of the active ingredients before or after administration to a human or an animal, such as, but not limited to, affecting delivery, release, adsorption, degradation, excretion, and the like. It is to be understood that inactive ingredients can affect the characteristics of the composition, such as, but not limited to, taste, color, smell, texture, integrity, mechanical properties, solubility, and the like. It is to be also understood that inactive ingredients can confer novel and advantageous properties on the composition and method of its use.

In a preferred embodiment, the active ingredients in the composition are melatonin, folic acid, riboflavin, cobalamin and pyridoxine. Melatonin is a product of the pineal gland and is also referred to as melatonin, N-acetyl-5-methoxytryptamine, 5-methoxy-N-acetyltryptamine, N-[2-(5-methoxy-1H-indol-3-yl)ethyl], 3-(N-Acetyl-2-aminoethyl)-5-methoxy indole, or N-[2-(5-Methoxy-1H-indol-3-yl]. Melatonin has the empirical formula $C_{13}H_{16}N_2O_2$. The chemical structure of melatonin is provided below:

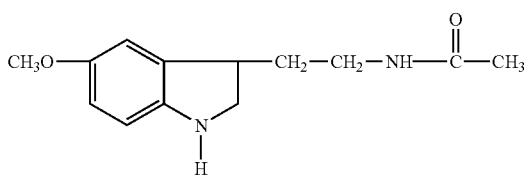

Folic acid is a member of the vitamin B complex and is the collective term for pteroylglutamic acids and their oligoglutamic acid conjugates. The term "folic acid" includes folate, which is a salt or ester of folic acid. The best dietary sources of folic acid are liver, brewer's yeast, and dark green leafy vegetables. Folic acid is easily lost when foods are improperly stored for too long, overcooked, overheated, or reheated.

Riboflavin is also known as vitamin $B_2$. Small amounts of riboflavin are distributed in a number of foods. The most concentrated riboflavin sources are milk products, liver, and dark green vegetables. Riboflavin is easily destroyed in the presence of light or baking soda.

Cobalamin is also known as cobalamin, cyanocobalamin or vitamin $B_{12}$. Foods of animal origin and fermented vegetables are the only dietary sources of cobalamin. Some vitamin loss occurs at cooking temperatures above 100 degrees Centigrade.

Pyridoxine is also known as pyridoxal, pyridoxamine or vitamin $B_6$. The best sources of pyridoxine are protein rich foods. These include lean-meat, wheat germ, brewer's yeast, poultry, fish, soybeans, cooked dry beans, peas, and peanuts. As much as 70 percent of the vitamin is lost when cooking water is discarded or foods are frozen.

The preferred dose for administration of the composition to a human or animal is adjusted to suit the human or animal to whom the composition is administered, and the purposes of a particular method during which the composition is administered, and varies with certain factors such as health, age, weight and metabolism of the human or the animal.

The preferred concentration of melatonin in the composition is from approximately 0.1 to 20 mg; the preferred concentration of folic acid in the composition is from 0.1 to 20 mg; the preferred concentration of riboflavin in the composition is from approximately 1 to 300 mg; the preferred concentration of cobalamin, if present in the composition, is from approximately 1 to 3000 micrograms (mcg); and the preferred concentration of pyridoxine, if present in the composition, is 2 to 50 mg. More preferably, the concentration of melatonin is from approximately 0.1 to less than 5 mg; the preferred concentration of folic acid is from approximately 0.4 to 10 mg; the preferred concentration of riboflavin is from approximately 100 to 200 mg; the preferred concentration of cobalamin is from approximately 6 to 200 mcg; and the preferred concentration of pyridoxine is from approximately 15 to 35 mg. Most preferably, the nutritional composition contains 1 mg melatonin, 2.5 mg folic acid, 150 mg riboflavin, 50 mcg cobalamin; and 25 mg pyridoxine.

Exemplary Formulations

In a preferred embodiment, the composition contains less than 5 mg of melatonin. The exemplary compositions are as follows:

| Composition 1 | Composition 2 | Composition 3 |
| --- | --- | --- |
| Melatonin 1 mg | Melatonin 3 mg | Melatonin 3 mg |
| Folic acid 2.5 mg | Folic acid 2.5 mg | Folic acid 2.5 mg |
| Riboflavin 150 mg | Riboflavin 150 mg | Riboflavin 150 mg |
| Cobalamin 50 mcg | Cobalamin 50 mcg | Cobalamin 2.5 mg |
| Pyridoxine 25 mg | Pyridoxine 25 mg | Pyridoxine 25 mg |

The exemplary compositions may further comprise inactive ingredients, such as, but not limited to: inulin (a diluent); crospovidone (a disintegrant); magnesium stearate (a lubricant), or combinations thereof. The exemplary compositions may further comprise shells, such as hypromellose capsule shells.

One embodiment of the composition is formulated as follows:
Melatonin 3 mg
Folic acid 2.5 mg
Riboflavin 150 mg
Cobalamin 2.5 mg
Pyridoxine 25 mg
Inulin 62 mg (diluent)
Crospovidone 6 mg (disintegrant)
Magnesium Stearate 1.25 mg (lubricant)
Hypromellose capsule shell 1 each The exemplary compositions are available as both rapid release and time-delayed release forms. For examples, the compositions are available as rapid release and delayed release capsules. The time-delayed formulation may utilize enteric coating process of the active ingredients to avoid rapid first-pass metabolism by the liver, thus ensuring more active ingredient to the target site, such as brain. In an adult human, melatonin has a relatively short half-life of approximately 45 minutes. Enteric coating ensures a delayed release of active ingredients. In turn, delayed release leads to longer duration of melatonin action in an individual, thus facilitating both sleep induction and sleep maintenance. As an example, a time-delayed release formulation may have a cellulose based or a beta-carotene based coating, or a combination thereof. It is to be understood, that the coatings are not limited to the foregoing and various coatings and delivery ingredients, or combination of those, may be used in the compositions provided herein to achieve the desired pattern of release when administered to a human or an animal.

Drug Delivery

The term "delivery vehicle" is a composition that contains one or more active agents and is designed to release the active agent in a particular fashion, either by immediately dispersing the agents in the digestive system, or by releasing the agents in a slow sustained fashion. The term encompasses porous microspheres, microcapsules, cross-linked porous beads, and liposomes that contain one or more active ingredients sequestered within internal cavities or porous spaces. The term also includes osmotic delivery systems, coated tablets or capsules that include nonporous microspheres, microcapsules, and liposomes, and active agents dispersed within polymeric matrices. A dosage form can include one or more delivery vehicles.

"Controlled" or "sustained" or "time release" delivery are equivalent terms that describe the type of active agent delivery that occurs when the active agent is released from a delivery vehicle at an ascertainable and manipulatable rate over a period of time, which is generally on the order of minutes, hours or days, typically ranging from about thirty minutes to about three days, rather than being dispersed immediately upon entry into the digestive tract or upon contact with gastric fluid. A controlled release rate can vary as a function of a multiplicity of factors. Factors influencing the rate of delivery in controlled release include the particle size, composition, porosity, charge structure, and degree of hydration of the delivery vehicle and the active ingredient(s), the acidity of the environment (either internal or external to the delivery vehicle), and the solubility of the active agent in the physiological environment, i.e., the particular location along the digestive tract.

"Targeted" or "site-specific" delivery means that the pharmaceutical preparation is formulated to limit the release of its contents in an amount appropriate to the site where release occurs. The term refers in particular to the active agent, whose site-specific delivery implements the performance of the therapeutic function at a specific site within the body of the subject to whom the preparation is administered.

Therapeutically Effective Amount

The phrase "therapeutically effective amount" means an amount sufficient to produce a therapeutic result. Generally the therapeutic result is an objective or subjective improvement of a disease or condition, achieved by inducing or enhancing a physiological process, blocking or inhibiting a physiological process, or in general terms performing a biological function that helps in or contributes to the elimination or abatement of the disease or condition.

As used herein, the term, "unit dosage form" refers to a composition intended for a single administration to treat a subject suffering from a disease or medical condition. Each unit dosage form typically comprises each of the active ingredients of this invention plus pharmaceutically acceptable excipients. Examples of unit dosage forms are individual tablets, individual capsules, bulk powders, and liquid solutions, emulsions or suspensions. Treatment of the disease or condition may require periodic administration of unit dosage forms, for example: one unit dosage form two or more times a day, one with each meal, one every four hours or other interval, or only one per day. The expression "oral unit dosage form" indicates a unit dosage form designed to be taken orally.

In a preferred embodiment, unit dosage forms of the melatonin compositions are consumed orally, including but not limited to tablets, capsules, pills, lozenges, wafers, powders, liquids, emulsions, suspensions, solutions and the like. However, compositions administered by other routes of administration, such as nasal sprays, patches, and suppositories and are also envisioned and fall within the scope of the present invention. Alternatively, the composition is included in a food or a beverage, such as, but not limited to, a dietary supplement bar or shake.

The composition is administered by any appropriate route, including but not limited to, orally (e.g. buccally or sublingually), transcutaneously or transdermally, rectally, as a suppository or an enema, topically, parenterally, subcutaneously sub-dermally intramuscularly, intraperitoneally, intravesicularly, intraarticularly, intravenously, intradermally, intracranially, intralesionally, intrathecally, intratumorally, intraocularly, ocularly, aerosolically, intrapulmonaryly, intraspinally, intraprostaticaly, sublingually, or by placement within cavities of the body, nasal inhalation, pulmonary inhalation, impression into the skin and electroporation, intrauterinaly, vaginally, into a body cavity, surgically administered, or administered into the lumen or parenchyma of an organ, and into bone marrow. Techniques useful in the various forms of administrations mentioned above include but are not limited to, topical application, ingestion, surgical administration, injections, sprays, transdermal delivery devices, osmotic pumps, electrodepositing directly on a desired site, or other means familiar to one of ordinary skill in the art. Sites of application can be external, such as on the epidermis, or internal, for example a joint capsule, or elsewhere. The preferred method of administration is by oral administration of a tablet.

The phrase "substantially homogeneous," when used to describe a formulation (or portion of a formulation) that contains a combination of components, means that the components, although each may be in particle or powder form, are fully mixed so that the individual components are not divided into discrete layers or form concentration gradients within the formulation.

The dosage forms of the composition provided herein are formulated for administration at various rates. Administration of one dosage form prior to a desired period of sleep is preferred.

A slower, more sustained release of the active agents can be achieved by placing the active agents in one or more delivery vehicles that inherently retard the release rate. Examples of such delivery vehicles include polymeric matrices that maintain their structural integrity for a period of time prior to dissolving, or that resist dissolving in the stomach but are readily made available in the post-gastric environment by the alkalinity of the intestine, or by the action of metabolites and enzymes that are present only in the intestine. The preparation and use of polymeric matrices designed for sustained drug release is well known. Examples are disclosed in U.S. Pat. No. 5,238,714 (Aug. 24, 1993) to Wallace et al.; Bechtel, W., *Radiology* 161: 601-604 (1986); and Tice et al., EPO 0302582 (Feb. 8, 1989).

Selection of the most appropriate polymeric matrix for a particular formulation can be governed by the intended use of the formulation. Preferred polymeric matrices are hydrophilic, water-swellable polymers such as hydroxymethylcellulose, hydroxypropylcellulose, hydroxyethylcellulose, hydroxymethylpropylcellulose, polyethylene oxide, and porous bioerodible particles prepared from alginate and chitosan that have been ionically crosslinked.

A delayed, post-gastric, prolonged release of the active ingredients in the small intestine (duodenum, ileum, jejunum) can also be achieved by encasing the active agents, or by encasing hydrophilic, water-swellable polymers containing the active agents, in an enteric (acid-resistant) film. One class of acid-resistant agents suitable for this purpose is that disclosed in Eury et al., U.S. Pat. No. 5,316,774 entitled "Blocked Polymeric Particles Having Internal Pore Networks for Delivering Active Substances to Selected Environments". The formulations disclosed in this patent consist of porous particles whose pores contain an active ingredient and a polymer acting as a blocking agent that degrades and releases the active ingredient upon exposure to either low or high pH or to changes in ionic strength. The most effective enteric materials include polyacids having a $pK_a$ of from about three to five. Examples of such materials are fatty acid mixtures, methacrylic acid polymers and copolymers, ethyl cellulose, and cellulose acetate phthalates. Specific examples are methacrylic acid copolymers sold under the name EUDRAGIT®, available from Rohm Tech, Inc., Maiden, Mass., U.S.A.; and the cellulose acetate phthalate latex AQUATERIC®, available from FMC Corporation, New York, N.Y., U.S.A., and similar products available from Eastman-Kodak Co., Rochester, N.Y., U.S.A.

Acid-resistant films of these types are particularly useful in confining the release of magnesium lactate and magnesium citrate to the post-gastric environment. Acid-resistant films can be applied as coatings over individual particles of the components of the formulation, with the coated particles then optionally compressed into tablets. An acid-resistant film can also be applied as a layer encasing an entire tablet or a portion of a tablet where each tablet is a single unit dosage form.

The compositions may conveniently be presented in unit dosage form and may be prepared by conventional pharmaceutical techniques. Such techniques include the step of bringing into association the compositions containing the active ingredient and one or more pharmaceutical carriers or excipients, in liquid or solid form, in a single dose or a dose repeated after a certain time interval. Therefore, the dosage forms of the composition optionally include one or more suitable and pharmaceutically acceptable excipients, such as, but not limited to, ethyl cellulose, cellulose acetate phthalates, mannitol, lactose, starch, magnesium stearate, sodium saccharin, talcum, glucose, sucrose, carbonate, and the like. These excipients serve a variety of functions, as indicated above, as carriers, vehicles, diluents, binders, and other formulating aids.

Embodiments of the present invention include methods for regulating sleep or circadian rhythms in a human or animal comprising administering to the human or animal novel nutritional compositions provided herein. The methods of regulating sleep or circadian rhythms provided herein include methods of inducing sleep and method of maintaining sleep, or both. The methods can also advantageously regulate the ability of a human or an animal to be awake or alert, or both, during waking hours, to fall asleep, wake up, or both, on a desired schedule. Also included within the embodiments of the present invention are methods of regulating a biological response of a human or an animal to melatonin comprising administering to the human or animal novel compositions disclosed herein. A method of modulating activity of melatonin in a nutritional composition, comprising combining melatonin and a vitamin in the composition, is also included within the embodiments of the present invention. A method of advantageously affecting synthesis or utilization, or both, of melatonin in a human or an animal, comprising administering novel compositions disclosed herein, is also within the embodiments of the present invention.

All publications, patent applications, patents, and other cited references and documents mentioned herein are incorporated by reference in their entirety.

The foregoing description is provided for describing and disclosing various and preferred embodiments of the present invention, and numerous modifications or alterations may be made without departing from the spirit and the scope of the invention.

What is claimed is:

1. A composition for regulating sleep or circadian rhythms in a human or in an animal, comprising less than 5 mg of melatonin per unit dosage form, 0.4 mg-10 mg of folic acid, 100 mg-200 mg of riboflavin, 0.001 mg-3 mg of cobalamin, and 15-35 mg of pyridoxine.

2. The composition of claim 1, comprising between 0.001 mg to 3 mg of cobalamin per unit dosage form.

3. The composition of claim 1, comprising between 2 mg to 3 mg of cobalamin per unit dosage form.

4. The composition of claim 1, comprising between 15 mg to 35 of pyridoxine per unit dosage form.

5. The composition of claim 1, comprising between 0.4 mg to 10 mg of folic acid per unit dosage form.

6. The composition of claim 1, comprising between 100 mg to 200 mg of riboflavin per unit dosage form.

7. The composition of claim 1, comprising 3 mg of melatonin per unit dosage form.

8. The composition of claim 1, comprising 1 mg melatonin per unit dosage form.

9. The composition of claim 1, comprising 3 mg of melatonin, 2.5 mg of folic acid, 150 mg of riboflavin, 2.5 of cobalamin and 25 mg pyridoxine per unit dosage form.

10. The composition of claim 1, further comprising an inactive ingredient, wherein the inactive ingredient is inulin, crospovidone, magnesium stearate, hypromellose or combinations thereof.

11. The composition of claim 1, wherein the composition is a rapid release composition, a delayed release composition, or a composition thereof.

12. The composition of claim 1, further comprising a coating.

13. The composition of claim 12, wherein the coating comprises cellulose beta-carotene, or a combination thereof.

14. A method for regulating sleep or circadian rhythms in a human or animal comprising administering to the human or animal a nutritional composition comprising less than 5 mg of melatonin per unit dosage form, 0.4 mg-10 mg of folic acid, 100 mg-200 mg of riboflavin, 0.001 mg-3 mg of cobalamin, and 15-35 mg of pyridoxine.

15. The method of claim 14 wherein the composition comprises between 0.001 mg to 3 mg of cobalamin per unit dosage form.

16. The method of claim 14, wherein the composition comprises between 2 mg to 3 mg of cobalamin per unit dosage form.

17. The method of claim 14, wherein the composition comprises between 15 mg to 35 mg of pyridoxine per unit dosage form.

18. The method of claim 1, wherein the composition comprises between 0.4 mg to 10 mg of folic acid per unit dosage form.

19. The method of claim 14, wherein the composition comprises between 100 mg to 200 mg of riboflavin per unit dosage form.

20. The method of claim 14, wherein the composition comprises 3 mg of melatonin, 2.5 mg of folic acid, 150 mg of riboflavin, 2.5 of cobalamin and 25 mg pyridoxine per unit dosage form.

21. The method of claim 14, wherein regulating sleep is inducing sleep or maintaining sleep.

22. A method of regulating a biological response of a human or an animal to melatonin comprising administering to the human or animal a composition comprising less than 5 mg of melatonin per unit dosage form, 0.4 mg-10 mg of folic acid, 100 mg-200 mg of riboflavin, 0.001 mg-3 mg of cobalamin, and 15-35 mg of pyridoxine.

23. The method of claim 22, wherein the biological response is the induction of sleep or an ability to remain asleep.

* * * * *